United States Patent [19]

Georgiev et al.

[11] Patent Number: 4,785,117
[45] Date of Patent: Nov. 15, 1988

[54] 5,5-DISUBSTITUTED-3-PHENYL-3-PHENYL-3-[(1H-IMIDAZOL-1-YLMETHYL) OR (1H-1,2,4-TRIAZOL-1-YLMETHYL)]-2-METHYLISOXAZOLIDINE DERIVATIVES (IR 3012)

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,701

[22] Filed: Oct. 2, 1987

[51] Int. Cl.$^4$ .................. A01N 43/52; A01N 43/653; C07D 233/60; C07D 249/08
[52] U.S. Cl. .................... 548/240; 548/341; 548/265
[58] Field of Search ......................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS 171137 2/1986 European Pat. Off. ............ 548/215
5476579 6/1979 Japan.

OTHER PUBLICATIONS

Kelly, R. C. et al., Chemical Abstract 93:114498u (1980), Abstracting German Offen. 2,918,878 (Nov. 22, 1979).
Haken, P. T. et al., Chemical Abstract 93:132471j (1980) Abstracting Brit. Pat. Appln. 2,024,218 (Jan. 9, 1980).
Takahi, Y. et al., Chemical Abstract 81:22233c (1974) Abstracting Japan Kokai 7399,336 (Dec. 15, 1973).
Boyce, C. B. et al., Chemical Abstract 87:23258a (1977), Abstracting German Offen. 2,639,189 (Mar. 10, 1977).
Funaki, Y. et al., Chemical Abstract 92:128915u (1980), Abstracting Japan Kokai 79 76,579 (Jun. 19, 1979).
Sokolov, S. V., et al., Chemical Abstract 55:7399 (1961) Abstracting "Isoxazole Compounds III Synthesis of some isoxazolylazoles", Zhur. Obshchei Khim, 30, pp. 1781–1787 (1960).
Kano, H., et al., Chem. Abstract 62:9139a (1965), Abstracting French No. 1,376,432 (Oct. 23, 1964).
Kano, H. et al., Chemical Abstract 63:8367a (1965), Abstracting French No. 1,380,177 (Nov. 27 1964).

Primary Examiner—Donald G. Daus
Assistant Examiner—Mark W. Noel

[57] ABSTRACT 5,5-Disubstituted-3-phenyl-3-[(1H-imidazol-1-ylmethyl) or (1H-1,2,4-triazol-1-ylmethyl)]-2-methylisoxazolidine derivatives are useful as antifungal agents.

6 Claims, No Drawings

5,5-DISUBSTITUTED-3-PHENYL-3-PHENYL-3-[(1H-IMIDAZOL-1-YLMETHYL) OR (1H-1,2,4-TRIAZOL-1-YLMETHYL)]-2-METHYLISOXAZOLIDINE DERIVATIVES (IR 3012)

BACKGROUND OF THE INVENTION

This invention pertains generally to substituted 2-methylisoxazolidines and more specifically to 5,5-disubstituted-3-phenyl-3-[(1H-imidazol-1-ylmethyl) or (1H-1,2,4-triazol-1-ylmethyl)]-2-methylisoxazolidines which are useful as antifungal agents.

BRIEF SUMMARY OF THE INVENTION

In accordance with this invention there are provided compounds of the formula:

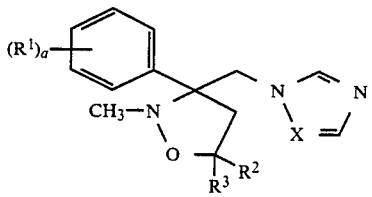

and the pharmaceutically acceptable acid addition salts thereof, in the form of their enantiomers or mixtures of their enantiomers including diastereomeric pairs of such enantiomers, wherein;

a = 1 or 2, $R^1$ is selected from hydrogen, halogen, lower alkyl and lower alkoxy groups and combinations thereof, provided that the ortho position is hydrogen, $R^2$ is selected from lower alkyl, phenyl, substituted phenyl and alkoxycarbonyl groups and $R^3$ is selected from lower alkyl, phenyl and substituted phenyl groups, wherein the phenyl substituents are selected from halogen, lower alkyl, and lower alkoxy groups and combinations thereof, and X is selected from CH or N.

DETAILED DESCRIPTION OF THE INVENTION

The compounds of the invention are useful as antifungal agents. They have in vitro activity against yeast and systemic mycoses and dermatophytes as determined by broth and agar testing techniques [(McGinnis, M. R., *Laboratory Handbook of Medical Mycology*, Academic Press, New York, N.Y. (1980)]. The compounds prepared in Examples 1 and 3 were found to have good to moderate inhibitory activity against a broad spectrum of organisms including Trichophyton mentagrophytes, Trichophyton rubrum, Trichophyton tonsurans, Epidermophyton floccosum, Miscrosporum canis, Aspergilus fumigatus, Candida albicans and Candida Stellatoidea. The minimum inhibitory concentrations, MIC, of the compounds of this invention ranged between 0.2 and 70 μg/ml.

Because of their antifungal activity, the compounds of this invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm-blooded animals (1 to 20 percent active ingredient).

The compounds of this invention are those of the formula:

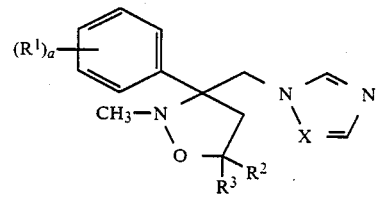

and the pharmaceutically acceptable acid addition salts thereof, in the form of their enantiomers or mixtures of enantiomers including diastereomeric pairs of such enantiomers, wherein, a = 1 or 2, R is selected from hydrogen, halogen, lower alkyl and lower alkoxy groups and combinations thereof, provided that ortho position is hydrogen, $R^2$ is selected from lower alkyl, phenyl, substituted phenyl and alkoxycarbonyl groups and $R^3$ is selected from lower alkyl, phenyl and substituted phenyl groups, wherein the phenyl rings can be substituted with one or more halogen, lower alkyl and lower alkoxy groups, and combinations thereof and X is selected from CH or N.

By halogen is meant chlorine, bromine, fluorine and iodine with chlorine and fluorine being preferred. By lower alkyl is meant alkyl groups containing one to four (1-4) carbons, by lower alkoxy is meant such groups containing one to six (1-6) carbons and by alkoxycarbonyl is meant ester groups containing alkyl radicals comprised of one to six (1-6) carbons. In either case alkyl radicals with three or more carbons can have a branched or unbranched chain. Preferably the substituted phenyl groups have one or two substituents.

The 5,5-disubstituted-3-phenyl-3-[(1H-imidazol-1-ylmethyl) or (1H-1,2,4-triazol-1-ylmethyl)]-2-methylisoxazolidine derivatives of this invention are obtained as a mixture of cis- and trans-diastereomers due to the presence of two asymmetric carbon atoms in the isoxazolidine ring. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The eluents may be used alone or in combinations, such as the ones comprised of 95–99% halogenated hydrocarbon and 1–5% alkanol by volume. The stereochemistry of the two asymmetric carbons atoms in the isoxazolidine ring may be determined by conventional methods that include x-ray crystallography, nuclear magnetic resonance spectroscopy, circular dichroism and optical rotatory dispersion. Both the cis- and trans-diastereomers are resolvable into their optical enantiomers with (+)- and (−)-optical rotations by standard techniques such as fractional recrystallization of the diastereomeric salts with optically active organic acids such as (+)- and (−)-tartaric acid, (+)- and (−)-dibenzoyltartaric acid and the like.

The compounds of this invention can be pepared as illustrated in the following diagram. The synthesis of the nitrone precursors 1 is accomplished by reacting an appropriately substituted 2-imidazolylacetophenone with N-methylhydroxylamine hydrochloride as described in our copending application Ser. No. 900,856 filed Aug. 27, 1986 whose disclosure is incorporated herein by reference. Subsequent reaction of the nitrone with an appropriate 1-alkene derivative 2 provides a diastereomeric mixture of the desired cis- and trans-5,5-disubstituted-3-phenyl-3-(1H-imidazol-1-ylmethyl)-2-methylisoxazolidine derivatives 3. Similarly by using a 2-(1H-1,2,4-triazol-1-yl)acetophenone the corresponding 3-(1H-1,2,4-triazol-1-ylmethyl)isoxazolidine derivatives can be prepared.

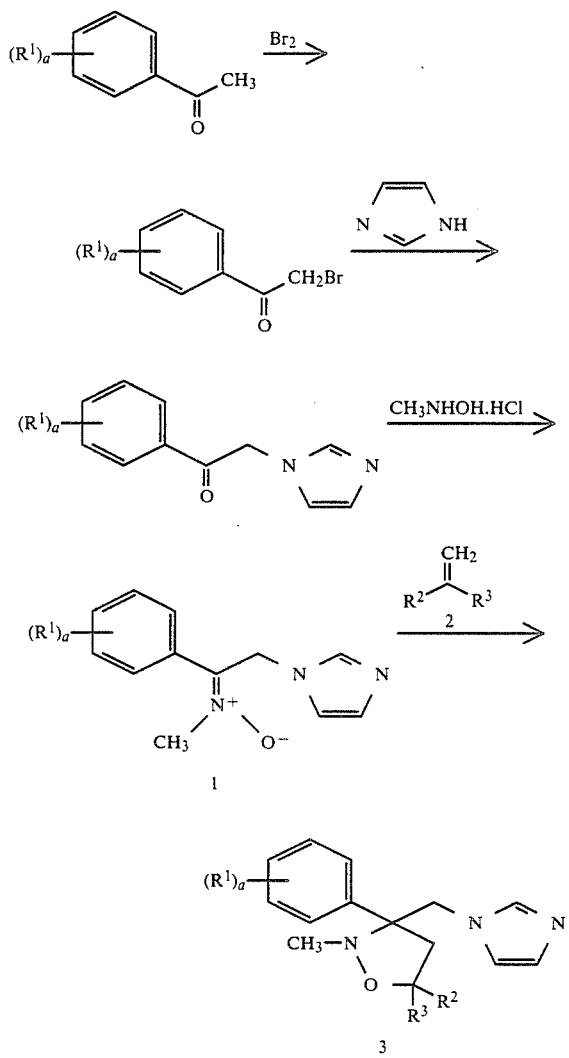

The compounds of this invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

5-(4-Chlorophenyl)-2,5-dimethyl-3-(1H-imidazol-1-ylmethyl)-3-phenylisoxazolidine (3, $R^1$=H, $R^2$=$CH_3$, $R^3$=$C_6H_4Cl$-4)

A solution of 10.79 g (0.0501 mol) of 2-(1H-imidazol-1-yl)-N-methyl-1-phenylethanimine N-oxide (1, $R^1$=H) [which can be prepared by reacting 2-(1H-imidazol-1-yl)-4′-chloroacetophenone (45.05 g, 0.204 mol), N-methylhydroxylamine hydrochloride (20.93 g, 0.251 mol) and sodium acetate (41.13 g, 0.502 mol) in 550 ml ethanol] and 8.72 g (0.0571 mol) of p-chloro-α-methylstyrene (2, $R^2$=$CH_3$, $R^3$=$C_6H_4Cl$-4) in 100 ml of toluene is heated to reflux and stirred under a nitrogen atmosphere for 70 hours. Upon cooling to ambient temperature, the reaction mixture is extracted with water (2×100 ml), and the organic layer is dried over anhydrous magnesium sulfate, then concentrated in vacuo. The residual dark oil, containing a cis- and trans-diastereomeric mixture of compound 3 ($R^1$=H, $R^2$=$CH_3$, $R^3$=$C_6H_4Cl$-4), is flashchromatographed on neutral silica gel using ethyl acetate as eluent. Isomer A (2.35 g, 12.7%) has a melting point of 180°–182° C. (ethyl acetate). Anal. Calcd. for $C_{21}H_{22}ClN_3O$: C, 68.56; H, 6.03; Cl, 9.64; N, 11.42. Found: C, 68.42; H, 6.05; Cl, 9.75; N, 11.40.

Isomer B (2.26 g, 12.2%) has a melting point of 122°–124° C. (ethyl ether). Anal. Calcd. for $C_{21}H_{22}ClN_3O$: C, 68.56; H, 6.03; Cl, 9.64; N, 11.42. Found: C, 68.61; H, 6.17; Cl, 9.69; N, 11.28.

EXAMPLE 2

3-(1H-Imidazol-1-ylmethyl)-2-methyl-3,5,5-triphenylisoxazolidine (3, $R^1$=H, $R^2$=$R^3$=$C_6H_5$)

Compound 3 ($R^1$=H, $R^2$=$R^3$=$C_6H_5$) is prepared by a method similar to that described in Example 1 from 6.46 g (0.030 mol) of 2-(1H-imidazol-1-yl)-N-methyl-1-phenylethanimine N-oxide (1, $R^1$=H) and 6.50 g (0.035 mol) of 1,1-diphenylethylene (2, $R^2$=$R^3$=$C_6H_5$) in 300 ml of toluene, followed by flash chromatography on neutral silica gel using a 97:3 by volume mixture of chloroform and methanol as the eluent.

Compound 3 ($R^1$=H, $R^2$=$R^3$=$C_6H_5$) (1.00 g, 8.4%) has a melting point of 183°–184° C. (ethyl acetate). Anal. Calcd. for $C_{26}H_{25}N_3O$: C, 78.96; H, 6.37; N, 10.62. Found: C, 78.61; H, 6.44; N, 10.57.

EXAMPLE 3

Methyl 3-(4-Chlorophenyl)-2,5-dimethyl-3-(1H-imidazol-1-ylmethyl)isoxazolidine-5-carboxylate (3, $R^1$=4-Cl, $R^2$=$CH_3$, $R^3$=$CO_2CH_3$)

Compound 3 ($R^1$=4-Cl, $R^2$=$CH_3$, $R^3$=$CO_2CH_3$) is prepared by a method similar to that described in Example 1 from 7.04 g (0.0282 mol) of 1-(4-chlorophenyl)-2-(1H-imidazol-1-yl)-N-methylethanimine N-oxide (1, $R^1$=4-Cl) and 4.0 ml (1.30 equiv) of methyl methacrylate (2, $R^2$=$CH_3$, $R^3$=$CO_2CH_3$). The resulting cis- and trans-diastereomeric mixture of compound 3 ($R^1$=4-Cl, $R^2$=$CH_3$) is flash-chromatographed on neutral silica gel using ethyl acetate as the eluent.

Isomer A (4.28 g, 43.4%) has a melting point of 119°–122° C. (ethyl acetate). Anal. Calcd. for $C_{17}H_{20}ClN_3O_3$: C, 58.37; H, 5.76; Cl, 10.13; N, 12.01. Found: C, 58.36; H, 5.74; Cl, 10.17; N, 11.98.

EXAMPLE 4

3-(Substituted phenyl)-2,5-dimethyl-3-(1H-imidazol-1-ylmethyl)-5-(substituted phenyl)isoxazolidines By following essentially the same methods as described for Example 1 and replacing (2-(1H-imidazol-1-yl)-N-methyl-1-phenylethanimine N-oxide by, b 2-(1H-imidazol-1-yl)-N-methyl-1-(4-methoxyphenyl)ethanimine N-oxide, or 2-(1H-imidazol-1-yl)-N-methyl-1-(4-methylphenyl)ethanimine N-oxide, or 2-(1H-imidazol-1-yl)-N-methyl-1-(4-chloro-3-methylphenyl)ethanimine N-oxide, or 2-(1H-imidazol-1-yl)-N-methyl-1-(4-fluorophenyl)ethanimine N-oxide, or 2-(1H-imidazole-1-yl)-methyl-1-(3,4-dichlorophenyl)ethanimine N-oxide, and replacing p-chloro-α-methylstyrene by,
α-methylstyrene, or
4-methyl α-methylstyrene, or
4-methoxy α-methylstyrene, or
3,4-dimethoxy α-methystyrene, or
3,4-dichloro α-methylstyrene, the corresponding 3-(substituted phenyl)-2,5-dimethyl-3-(1H-imidazol-1-ylmethyl)-5-(phenyl or substituted phenyl)isoxazolidines can be prepared.

For example, 3-(4-methoxyphenyl)-2,5-dimethyl-3-(1H-imidazol-1-ylmethyl)-5-phenylisoxazolidine, 5-(3,4-dichlorophenyl)-2,5-dimethyl-3-(1H-imidazol-1-ylmethyl)-3-(4-methoxyphenyl)isoxazolidine, 3-(4-methylphenyl)-2,5-dimethyl-3-(1H-imidazol-1-ylmethyl)-5-(4-methoxyphenyl)isoxazolidine, 3-(4-chloro-3-methylphenyl)-2,5-dimethyl-3-(1H-imidazol-1-ylmethyl)-5-(4-methylphenyl)isoxazolidine, 5-(3,4-dimethoxyphenyl)-2,5-dimethyl-3-(1H-imidazol-1-yl-methyl)-3-(4-methylphenyl)isoxazolidine.

EXAMPLE 5

5,5-Disubstituted 3-(phenyl or substituted phenyl)-2-methyl-3-(1H-1,2,4-triazol-1-ylmethyl)isoxazolidines By following essentially the same methods as decribed for examples 1–4 and substituting a 2-(1H-1,2,4-triazol-1-yl)-N-methyl-1-(phenyl or substituted phenyl)ethanimine N-oxide [prepared by reacting a 2-(1H-1,2,4-triazol-1-yl)acetophenone (or substituted acetophenone) with N-methylhydroxylamine hydrochloride] for 2-(1H-imidazol-1-yl)-N-methyl-1-(phenyl or substituted phenyl)ethanimine N-oxide, the corresponding 5,5-disubstituted-3-(phenyl or substituted phenyl)-2-methyl-3-(1H-1,2,4-triazol-1-ylmethyl)isoxazolidines can be prepared.

For example, 5-(4-chlorophenyl)-2,5-dimethyl-3-(1H-1,2,4-triazol-1-ylmethyl)-3-phenylisoxazolidine, 3-(1H-1,2,4-triazol-1-ylmethyl)-2-methyl-3,5,5-triphenylisoxazolidine, and methyl 3-(4-chlorophenyl)-2,5-dimethyl-3-(1H-1,2,4-triazol-1-ylmethyl)isoxazolidine-5-carboxylate.

Salts of the compounds of the invention can be prepared as known in the art, for example, by dissolving the compound in a 10:1 by volume mixture of ethanol and aqueous acid such as HCl or $HNO_3$, evaporating the solvent, and then recrystallizing the crude salt, for example, from methanol-ether, 1:3 by volume in the case of HCl salts, and ethanol in the case of $HNO_3$ salts.

We claim:

1. A compound of the formula:

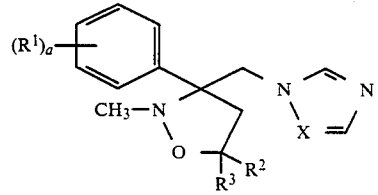

and the pharmaceutically acceptable acid addition salts thereof, in the form of their enantiomers or mixture of their enantiomers including diastereomeric pairs of such enantiomers, wherein;

a = 1 or 2, $R^1$ is selected from hydrogen, halogen, lower alkyl and lower alkoxy groups and combinations thereof, provided that the ortho position is hydrogen, $R^2$ is selected from lower alkyl, phenyl, substituted phenyl and alkoxycarbonyl groups and $R^3$ is selected from lower alkyl, phenyl and substituted phenyl groups, wherein the phenyl substituents are selected from one to three of halogen, lower alkyl, and lower alkoxy groups and combinations thereof, and X is selected from CH or N.

2. The compound of claim 1 wherein X=CH.

3. The compound of claim 1 wherein X=N.

4. The compound of claim 1 wherein the compound is 5-(4-chlorophenyl)-2,5-dimethyl-3-(1H-imidazol-1-ylmethyl)-3-phenylisoxazolidine.

5. The compound of claim 1 wherein the compound is 3-(1H-imidazol-1-ylmethyl)-2-methyl-3,5,5-triphenylisoxazolidine.

6. The compound of claim 1 wherein the compound is methyl 3-(4-chlorophenyl)-2,5-dimethyl-3-(1H-imidazol-1-ylmethyl)isoxazolidine-5-carboxylate.

* * * * *